United States Patent [19]

Kondo et al.

[11] 4,342,694
[45] * Aug. 3, 1982

[54] PROCESSES FOR PRODUCING PYRETHROID INSECTICIDE INTERMEDIATES

[75] Inventors: Kiyoshi Kondo; Toshiyuki Takashima; Minoru Suda, all of Kanagawa, Japan

[73] Assignee: FMC Corporation, Philadelphia, Pa.

[*] Notice: The portion of the term of this patent subsequent to Aug. 3, 1999, has been disclaimed.

[21] Appl. No.: 162,292

[22] Filed: Jun. 23, 1980

Related U.S. Application Data

[62] Division of Ser. No. 90,223, Nov. 1, 1979, Pat. No. 4,235,780.

[51] Int. Cl.$^3$ .................. C07D 309/30; C07D 307/93
[52] U.S. Cl. ........................... 549/273; 204/158 HA; 204/158 R; 560/17; 560/177; 562/431; 562/577; 549/302
[58] Field of Search .................... 260/343.5, 343.3 R; 204/158 HA, 158 R

[56] References Cited

U.S. PATENT DOCUMENTS 4,195,033  3/1980  Punja ............................. 260/343.6
4,215,050  7/1980  Lantzsch ....................... 260/343.6

OTHER PUBLICATIONS

March, Advanced Organic Chemistry, 2nd Edition, pp. 687 to 689 and pp. 746 to 747.
Osborn et al. J. Am. Chem. Soc. 90, 5806 (1968).

Primary Examiner—Jane T. Fan
Attorney, Agent, or Firm—Robert M. Kennedy; Robert L. Andersen; H. Robinson Ertelt

[57] ABSTRACT

Processes for producing a (1α, 4α, 5α)-6,6-dimethyl-4-halo-substituted-methyl-3-oxabicyclo[3.1.0]hexan-2-one and its novel intermediates from known and inexpensive starting materials are described and exemplified. The halomethyl bicyclic lactone is a useful intermediate for the preparation of insecticidal cis-3-(2,2-dihaloethenyl)-2,2-dimethylcyclopropanecarboxylates or cis-3-(2-halo-2-trihalomethylethenyl)-2,2-dimethylcyclopropanecarboxylates.

5 Claims, No Drawings

PROCESSES FOR PRODUCING PYRETHROID INSECTICIDE INTERMEDIATES

This is a division of application Ser. No. 090,223, filed Nov. 1, 1979, issued Nov. 15, 1980 as U.S. Pat. No. 4,235,780.

The present invention relates to (1) the preparation of a (1α, 4α, 5α)-6,6-dimethyl-4-halo substituted-methyl-3-oxabicyclo[3.1.0]hexan-2-one, referred to hereinafter as halomethyl bicyclic lactone, to (2) novel intermediates for production of the halomethyl bicyclic lactone, and to (3) various novel process steps by which the intermediates and the halomethyl bicyclic lactone are prepared from known and inexpensive starting materials.

The halomethyl bicyclic lactone is a useful intermediate for the production of insecticidal cis-3-(2,2-dihaloethenyl)-2,2-dimethylcyclopropanecarboxylates or cis-3-(2-halo-2-trihalomethylethenyl)-2,2-dimethylcyclopropanecarboxylates. An alternate process for preparing the halomethyl bicyclic lactone and its use as an insecticide intermediate is described in copending U.S. Ser. No. 000,736, filed Jan. 3, 1979.

A process for the production of a trihalomethyl bicyclic lactone is disclosed in Belgian Pat. No. 868,445, published Dec. 27, 1978. The process, illustrated by the chemical equations below, involves reacting the corresponding hydroxy bicyclic lactone, caronaldehydic acid, with a haloform, then cyclo-dehydrating the acid formed to produce the trihalomethyl bicyclic lactone.

Belgian 868,445

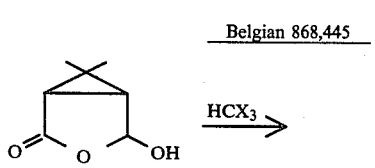

-continued
Belgian 868,445

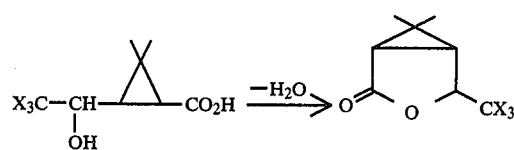

The disclosed process and intermediates of the Belgian Patent differ from the compounds and process of the present invention.

Various processes for preparing caronaldehydic acid, the hydroxy bicyclic lactone starting material in the process of the Belgian patent, are known in the art and are exemplified by the following chemical equations.

U.S. Pat. No. 3,723,469

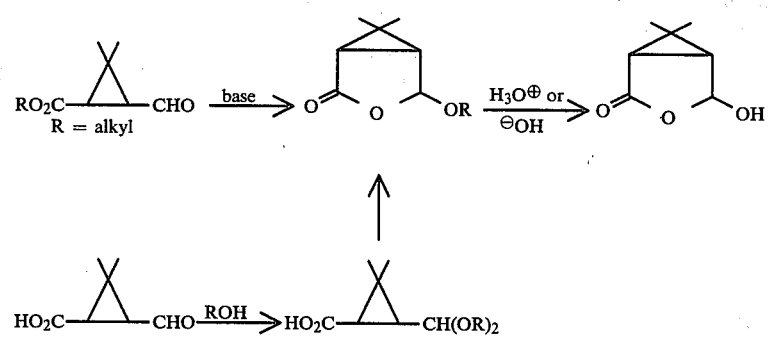

U.S. Pat. No. 4,132,717

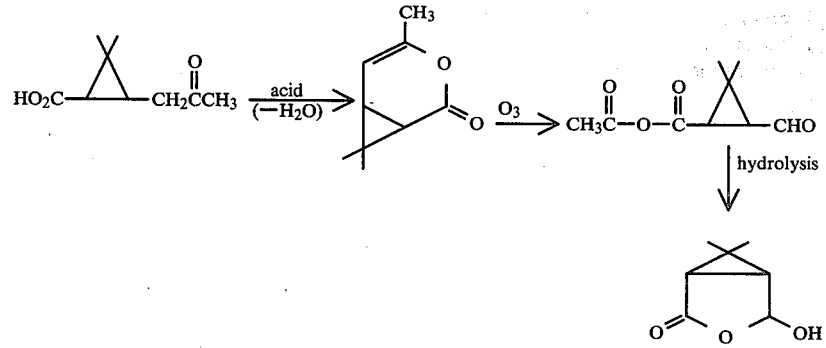

A feature common to the processes shown above for producing the bicyclic structure of caronaldehydic acid is the use of the cyclopropane derivative as starting material upon which the second ring is subsequently built. In the present invention, a cyclopropane ring is not formed until the last step in the overall process to a bicyclic lactone.

In accordance with the present invention there are provided novel compounds having the formulas:

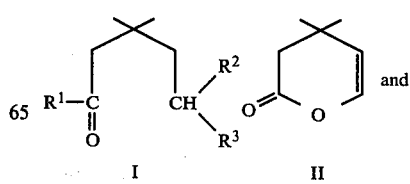

I  II

-continued

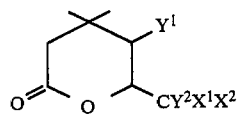

III and processes for preparing these compounds.

The following definitions are applicable in this application: "lower", as applied to an alkyl or alkoxy group, means having 1-6 carbon atoms, preferably 1-4 carbon atoms; "halo" or "halogen" means a fluorine, chlorine, or bromine atom which may be independently selected; and "aryl" means a phenyl radical which may be substituted with one or more halogen atoms and/or lower alkyl groups. These definitions apply throughout the specification and claims except where a contrary meaning is clearly indicated.

One aspect of the invention comprises a novel class of 3,3-dimethylpentanoyl derivatives of the formula:

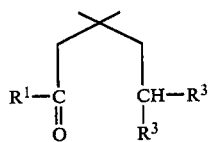

I wherein $R^1$ is a hydroxy group or the group —OR where R is a lower alkyl radical; $R^2$ is a hydrogen or chlorine atom; and $R^3$ is the group —$SR^4$ where $R^4$ is an aryl radical, preferably phenyl; or $R^2$ and $R^3$ are taken together and are an oxygen atom.

Other composition aspects of this invention comprise compounds of the formulas:

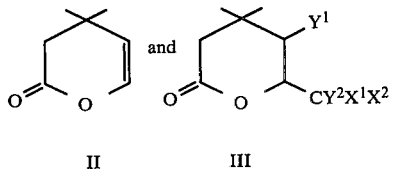

II   III $X^1$ and $X^2$ are the same or different and each is an independently selected halogen atom, a trichloromethyl group, or a trifluoromethyl group, and $Y^1$ and $Y^2$ are independently bromine, or chlorine atoms with the proviso that $Y^1$ is a bromine atom when at least one of $X^1$, $X^2$, and $Y^2$ is a bromine atom. In preferred compounds of formula III $X^1$ is a bromine or chlorine atom, particularly a chlorine atom, and $X^2$ is the same as $X^1$ or is a trifluoromethyl group.

Compounds of the formulas I, II, and III are useful intermediates for the production of a halomethyl bicyclic lactone of the formula:

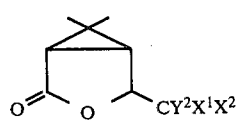

IV wherein $Y^2$, $X^1$ and $X^2$ are as defined for the compounds of formula III.

The process embodiments of the present invention relate to processes for the production of the compounds of formulas I, II, III and IV, and an overall process for the production of compounds of formula IV in which the compounds of formulas I, II, and III are intermediates.

The overall process comprises six basic steps and an alternate step. The overall process, each step including the alternate step, and all combinations of successive steps represent individual processes of the invention. These processes are illustrated by the chemical equations below. The product of each step, except step VI, is a novel composition of matter of the present invention. Each is a compound of formula I, II or III, and is numbered accordingly.

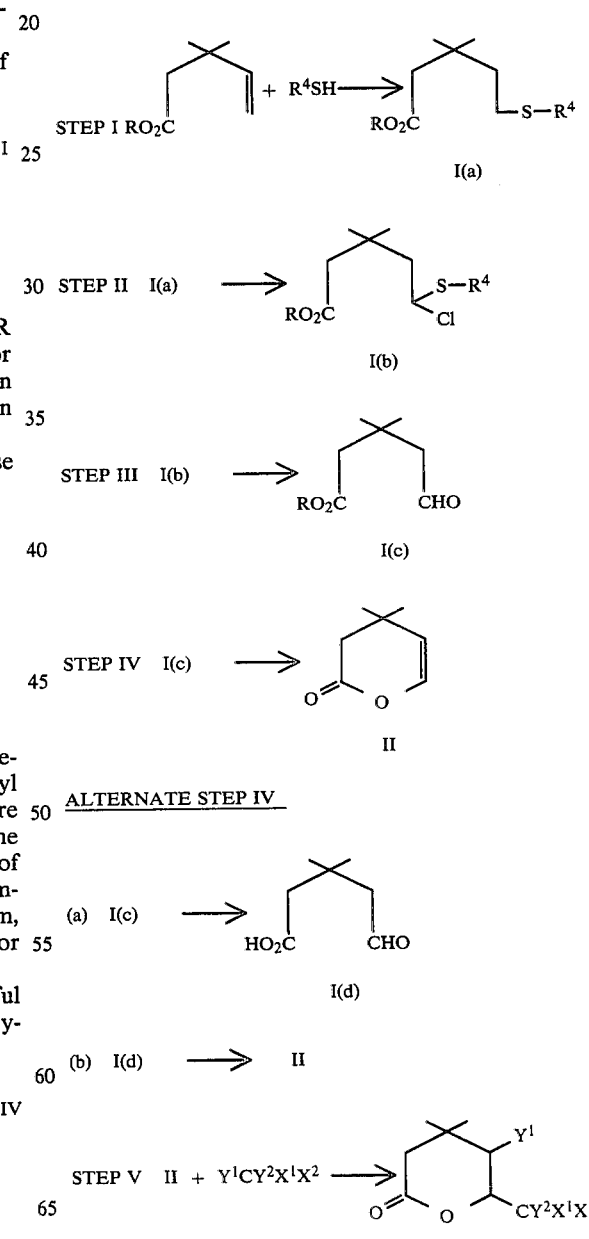

STEP VI III ⟶ 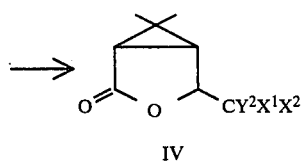

IV

STEP I

In one process aspect, step I above, the intermediate of formula I(a), a lower alkyl 3,3-dimethyl-5-arylthiopentanoate, is produced by the addition reaction of an aryl mercaptan and a lower alkyl 3,3-dimethyl-4-pentenoate.

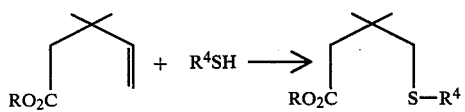

R is lower alkyl, conveniently ethyl or methyl. $R^4$ is an aryl group, preferably phenyl.

An initiator is required in step I to initiate the reaction, which is presumably a free radical addition reaction. Suitable initiators include light and free radical initiators such as acyl peroxides. Benzoyl peroxide has been found to be desirable and highly effective. When an acyl peroxide is employed, satisfactory results are obtained when the amount of peroxide used is in the range of about 0.5 mole % to about 6 mole % based on the pentenoate substrate. The acyl peroxide may conveniently be introduced into the reaction vessel in a single addition or portionwise in several additions throughout the course of the reaction. The use of light as an initiator generally gives poor results when it is employed alone. However, the use of light in conjunction with another initiator, particularly benzoyl peroxide, generally results in higher yields of the addition product than obtained with either initiator alone. An incandescent light bulb, advantageously of at least 50 watts, preferably of at least 100 watts, may be utilized as the light source.

The step I reaction is conducted at an elevated temperature, usually in the range of about 80° C. to 140° C., preferably 100° C. to 130° C. Under these conditions, a reaction time of from one to five days, generally four or five days, is usually sufficient. A solvent is generally not required in the reaction, but solvents which do not adversely affect the reaction or the product may be employed.

STEP II

A second process aspect of the present invention relates to step II in the overall process shown above. This step is illustrated by the chemical equation below wherein R and $R^4$ are as defined for step I.

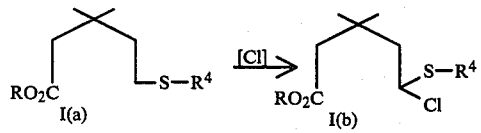

In this aspect, the lower alkyl 3,3-dimethyl-5-arylthiopentanoate I(a) is chlorinated to give the corresponding 5-arylthio-5-chloro compound I(b). Many chlorinating agents are known to be capable of chlorinating an alkyl aryl thioether in the α-position of the alkyl group and are expected to be suitable for use here. The use of 1-chloro-2,5-pyrrolidinedione is especially desirable since it usually does not require extensive product purification during workup.

The chlorination reaction is conducted at a temperature in the range of about −20° C. to 50° C., preferable 0° C. to 25° C., in an inert solvent. A particularly useful solvent is tetrahydrofuran or carbon tetrachloride. Other solvents which do not adversely affect the reaction are also suitable, and include dioxane, 1,2-dimethoxyethane, and chloroform. Generally, 4–8 ml of solvent for each gram of compound I(a) to be chlorinated is sufficient. With 1-chloro-2,5-pyrrolidinedione, the reaction is adequately complete within 2–9 hours, usually 3–4 hours, when the reaction temperature is in the range of about 5° C. to 20° C.

If the product of step II is to be carried forward in step III of the present overall process, it is usually not necessary that it be isolated and purified. Mere filtering of the step II reaction mixture affords a solution of the chlorinated product adequately pure for use per se in the step III reaction.

STEP III

Step III, illustrated by the chemical equation below, is a third process aspect of the present invention and relates to a process for producing a lower alkyl 3,3-dimethyl-5-oxopentanoate, I(c), by hydrolysis of the corresponding 5-arylthio-5-chloro derivative I(b).

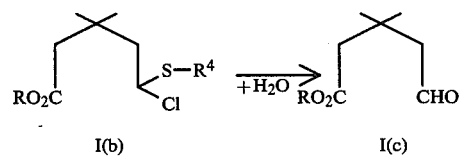

R and $R^4$ are as defined for step I.

The hydrolysis is effected in the presence of cupric oxide, cupric chloride, and water. Advantageously, equal parts by weight of cupric oxide and cupric chloride are used with from about 0.9 to 4 moles, preferably 1 mole, of cupric oxide being employed for each mole of sulfide to be hydrolyzed. At least one molar equivalent of water is required for the hydrolysis, based on the amount of material to be hydrolyzed. The use of an excess of water does not appear to critically interfere with the reaction.

The step III reaction is conducted in the presence of a solvent, which should be at least partially water soluble. Suitable solvents include diethyl ether, 1,2-dimethoxyethane, dioxane, tetrahydrofuran, acetone, and numerous other water soluble or partially water soluble solvents. Particularly useful solvents are acetone and tetrahydrofuran.

The hydrolysis can be conducted over a wide temperature range but is preferably conducted at a temperature in the range of from about 10° C. to 30° C., conveniently at room temperature.

STEP IV

A fourth process aspect of this invention relates to step IV of the overall process and provides for the production of 3,4-dihydro-4,4-dimethyl-2H-pyran- 2-one, the compound of formula II, by cyclization of a compound of formula I(c). R is as defined for step I.

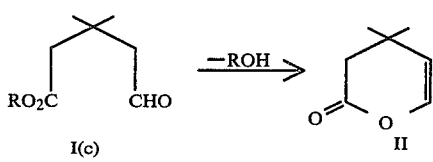

To effect the cyclization a cyclizing agent, preferably phosphoryl chloride, is required. While cyclizing agents such as benzoyl chloride, para-toluenesulfonic acid, paratoluenesulfonic acid hydrate, or a mixture of para-toluenesulfonic acid and acetic anhydride can be used, their use frequently favors a competing reaction in which a di-lower alkyl 3,3-dimethyl-1,5-dicarboxylate is formed. The diester by-product is formed to a lesser extent when phosphoryl chloride is used. Best results are obtained when from about 0.5 to 1.5 moles of cyclizing agent are used for each mole of I(c) to by cyclized.

The cyclization is conducted in the presence of a solvent, preferably sulfolane. Other solvents such as benzene, toluene, and dioxane can be used, but their use generally results in a lower yield of cyclized product II, and the formation of considerable diester by-product.

The reaction is conducted at elevated temperature, preferably in the range of about 110° C. to 225° C., more preferably 180° C. to 210° C. Under these temperature conditions a reaction time of 1 to 2 hours is usually sufficient.

ALTERNATE STEP IV

It will be evident to those skilled in the art that the dihydropyranone II can also be produced from 3,3-dimethyl-5-oxopentanoic acid, I(d), a novel and hitherto unavailable compound now accessible by hydrolysis of the 5-oxopentanoate I(c). This alternate route to compound II, which comprises the steps of (a) hydrolyzing the lower alkyl 3,3-dimethyl-5-oxopentanoate I(c) to give 3,3-dimethyl-5-oxopentanoic acid, I(d), and then (b) cyclizing the 3,3-dimethyl-5-oxopentanoic acid to form 3,4-dihydro-4,4-dimethyl-2H-pyran-2-one, II, is a fifth process aspect of this invention. R is lower alkyl in the formula below.

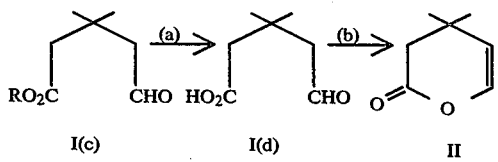

(a) Hydrolysis of the lower alkyl 3,3-dimethyl-5-oxopentanoate I(c) to give 3,3-dimethyl-5-oxopentanoic acid, I(d), is effected in acid or base, at a temperature advantageously in the range of about 20° C. to 50° C.

In a particularly effective method of hydrolysis, the ester I(c) is subjected to saponification using sodium hydroxide or potassium hydroxide, followed by acidification of the resulting sodium or potassium salt to form the free acid I(d). The reaction is facilitated by use of a mixture of methanol or ethanol and water for dissolution of the alkali metal hydroxide and the ester. If the hydrolysis is conducted at about 25° C., a reaction time of about 1 to 4 days, usually 1 to 2 days, is generally sufficient.

(b) For cyclization of the free acid I(d), a cyclizing agent, preferably thionyl chloride, is required. Other suitable cyclizing agents include phosphoryl chloride, benzoyl chloride, para-toluenesulfonic acid, para-toluenesulfonic acid hydrate, and a mixture of para-toluenesulfonic acid and acetic anhydride. The reaction is conducted at a temperature in the range of about 25° C. to 150° C., usually about 80° C. to 115° C., in an inert solvent, for example an aromatic hydrocarbon such as benzene, toluene or xylene. Typically, a solution of the acid I(d) and thionyl chloride (about 1 to 2 moles for each mole of I(d) is sufficient) in benzene is heated under reflux for up to about 24 hours, usually 5 to 8 hours.

STEP V

A sixth process aspect, step V of the overall process, provides for the production of the compound of formula III, a 5-bromo- or chloro-3,4,5,6-tetrahydro-4,4-dimethyl-6-halo substituted-methyl-2H-pyran-2-one, by a regiospecific free radical addition of a halomethane, $Y^1CY^2X^1X^2$, across the double bond of the dihydropyranone II. In the formulas below $X^1$ and $X^2$ are the same or different and each is an independently selected halogen atom, a trichloromethyl group, or a trifluoromethyl group, and $Y^1$ and $Y^2$ are independently bromine or chlorine atoms with the proviso that $Y^1$ is a bromine atom when at least one of $X^1$, $X^2$, and $Y^2$ is a bromine atom.

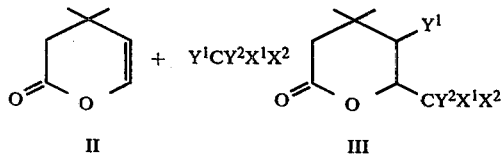

The reaction is conducted in the presence of an initiator selected from an acyl peroxide, light, and an acyl peroxide and light. Benzoyl peroxide is a preferred acyl peroxide. The light source may be an incandescent light bulb, advantageously of at least 50 watts, preferably of at least 100 watts. When an acyl peroxide is employed, it is advantageously used in an amount in the range of about 25 to 100 mole % based on the amount of the dihydropyranone II to be converted. It is also advantageous to add the acyl peroxide to the reaction vessel in several portions throughout the course of the reaction rather than in a single addition at the outset. Other free radical initiators such as azobisisobutyronitrile appear to be ineffective initiators for the reaction, particularly when a short reaction time is employed.

The use of a solvent, although generally not required, is desirable. A large molar excess of the halomethane may be used and will serve as the solvent. Other solvents which do not adversely affect the reaction or reaction product, for example, acetonitrile, alcohols, dimethylformamide, aliphatic hydrocarbons, aromatic hydrocarbons, and the like, are also suitable.

The reaction is conducted at an elevated temperature, preferably at a temperature in the range of about 50° C. to 200° C., more preferably at from 60° C. to 125° C.

The regiospecific addition of the free radial $.CY^2X^1X^2$ to C-6 of the dihydropyranone ring rather than to C-5 is surprising. It is known in the art that free radicals with the unpaired electron α to an OR group (C-6 of the dihydropyranone may be considered α to an OR group) have increased stability. See J. March, *Advanced Organic Chemistry*, Second Edition, P. 632, McGraw-Hill Book Co., New York, 1977, 1968. One would thus expect addition of $.CY^2X^1X^2$ to occur at C-5, resulting in an unpaired electron at C-6 which could be stabilized by resonance:

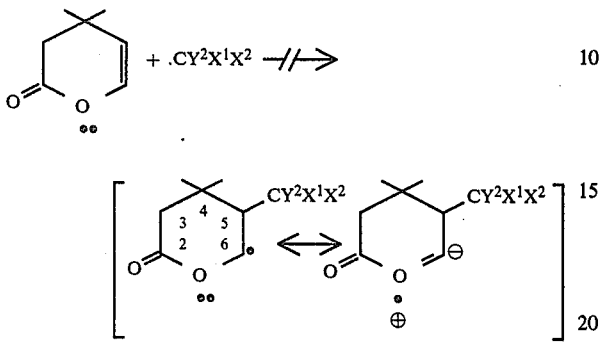

A possible explanation for the unexpected course of the reaction is that addition of $.CY^2X^1X^2$ to C-5 is sterically hindered by the presence of the gem-dimethyl group at C-4, and/or the expected resonance stabilization of an unpaired electron at C-6 because of its position adjacent to oxygen with its unbonded electrons, is diluted by the electron withdrawing carbonyl group at C-2 thereby minimizing its effect. It is known that steric hindrance can play a role in free radical addition, for example, the addition of a trichloromethyl radical to the exo side of norbornene; see "Steric Control in the Free Radical Addition of Carbon Tetrachloride to Norbornenes," C. L. Osborn et al., J. Am. Chem. Soc., 90, 5806 (1968). However, no reference has been found directly comparing steric effects and resonance stabilization in free radical addition reactions. Thus, the regiospecific addition of $.CY^2X^1X^2$ to C-6 of the dihydropyranone is unexpected since one could not have predicted in advance which course the reaction might take.

STEP VI

A seventh process aspect, step VI of the overall process, provides for the preparation of the halomethyl bicyclic lactone IV by dehydrohalogenation of the 5-bromo- or chloro-tetrahydropyranone of formula III, bringing about ring closure to form the bicyclic lactone. In the formulas below $Y^1$, $Y^2$, $X^1$, and $X^2$ are as defined for step V.

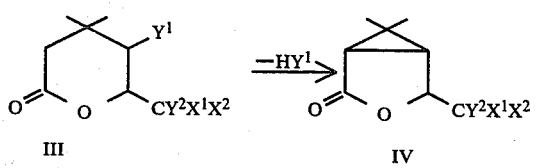

The dehydrohalogenation of III to give IV is effected by base. Effective bases include alkali metal hydrides and alkali metal alkoxides, particularly t-alkoxides such as the sodium or potassium salt of t-butanol or t-pentanol. Use of a sterically hindered base such as a sodium or potassium t-alkoxide, or a base that is an effective proton abstractor but not a particularly effective nucleophile such as sodium hydride is desirable and generally results in a higher yield of the halomethyl bicyclic lactone IV. Straight chain alkoxides will also effect the desired conversion but will usually enter into a competing reaction involving the C-2 carbonyl group of the substrate; the yield of desired product IV being reduced in proportion to the extent to which the competing reaction operates. The product of the competing reaction is an epoxide, exemplified by compound V in the following chemical equation which illustrates the reaction when sodium methoxide is employed as the base.

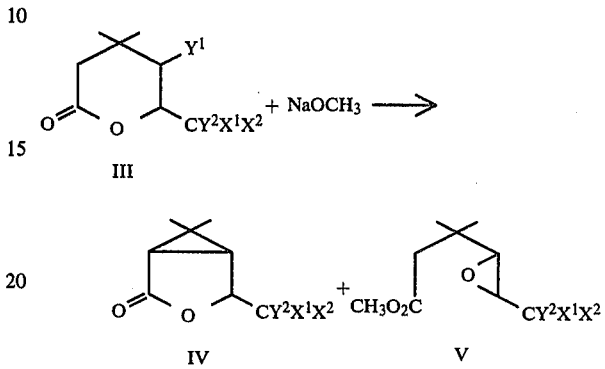

The reaction is conducted in the presence of a solvent, suitably non-hydroxylic, for example, an ether of 4-6 carbon atoms such as diethyl ether, dioxane, dimethoxy ethane or tetrohydrofuran, an aromatic hydrocarbon of 6 to 10 carbon atoms such as benzene or toluene, or an aliphatic hydrocarbon of 5 to 10 carbon atoms such as pentane, hexane or heptane. The use of tetrahydrofuran or toluene is preferred.

The dehydrohalogenation proceeds facilely at a temperature in the range of about $-40°$ C. to $30°$ C. The preferred temperature range is about $-10°$ C. to $10°$ C.

The present invention is illustrated in greater detail by the following examples. Temperatures are in degrees Celsius and pressures are in mm Hg and/or Pa. Unless otherwise specified, concentration of liquid volume was carried out under the reduced pressure produced by a water aspirator. Purity determinations were made by gas liquid phase chromatography (glpc). Tetramethylsilane was employed as an internal standard for the nmr spectra. In reporting the nmr data the abbreviations have the following significance: s, singlet; d, doublet; t, triplet; q, quartet; m, multiplet. Any of the abbreviations may be preceded by b for broad or d for double, for example, b.s., broad singlet.

Example 1 illustrates the preparation of a compound of formula I(a) by the process of step I.

EXAMPLE 1

Preparation of ethyl 3,3-dimethyl-5-phenylthiopentanoate

A mixture of 60.0 g (0.384 mole) of ethyl 3,3-dimethyl-4-pentenoate and 90.0 g (0.817 mole) of benzenethiol was irradiated with a 100 watt incandescent light bulb at 120°–130° C. for 4 days. Benzoyl peroxide (1.8 g, 0.0074 mole) was added to the reaction vessel in 300 mg increments at various times throughout the 4-day irradiation period for a total of six such additions. Distillation of the reaction mixture gave 102.3 g (96% yield) of ethyl 3,3-dimethyl-5-phenylthiopentanoate, 96.3% purity (glpc), hp 130° C./27 Pa (0.2 mm Hg).

Methyl 3,3-dimethyl-5-phenylthiopentanoate, 97.1% purity (glpc), bp 130° C./40 Pa (0.3 mm Hg), was prepared by the procedure of Example 1 in 92% yield.

Example 2 illustrates the preparation of a compound of formula I(b) by the process of step II.

EXAMPLE 2

Preparation of ethyl 5-chloro-3,3-dimethyl-5-phenylthiopentanoate

To a solution of 1.06 g (3.09 mmol) of ethyl 3,3-dimethyl-5-phenylthiopentanoate in 10 mL of carbon tetrachloride was added 590 mg (4.4 mmol) of 1-chloro-2,5-pyrrolidinedione, and the mixture was stirred at room temperature for 2 hours. The mixture was filtered, and the filtrate concentrated to give ethyl 5-chloro-3,3-dimethyl-5-phenylthiopentanoate as an oil. The product was used without further purification in the reaction described in Example 3 below. NMR Data (CDCl$_3$):

δ(ppm): 1.10 (6H, s), 1.20 (3H, t), 2.10 (2H, d), 2.25 (2H, s), 4.02 (2H, g), 5.23 (1H, t), 7.00–7.53 (5H, m).

Example 3 illustrates the preparation of a compound of formula I(c) by the process of step III.

EXAMPLE 3

Preparation of ethyl 3,3-dimethyl-5-oxopentanoate from ethyl 5-chloro-3,3-dimethyl-5-phenylthiopentanoate The crude ethyl 5-chloro-3,3-dimethyl-5-phenylthiopentanoate from Example 2 was dissolved in 15 mL of acetone, and the solution was added to a mixture of 1.2 g (8.9 mmol) of cupric chloride and 1.2 g (15 mmol) of cupric oxide in 15 mL of acetone and 0.6 mL of water. The mixture was stirred at room temperature for 30 minutes, filtered, and the filtrate concentrated to give a residue. The residue was dissolved in methylene chloride, and the solution washed successively with an aqueous sodium bicarbonate solution and an aqueous solution of sodium chloride. The organic layer was separated, dried over anhydrous magnesium sulfate, filtered, and the filtrate concentrated to give 1.0 g of ethyl 3,3-dimethyl-5-oxopentanoate.

NMR Data (CCl$_4$): δ(ppm): 1.11 (6H, s), 1.23 (3H, t), 2.32 (2H, s), 2.45 (2H, b.s.), 4.05 (2H, g), 9.72 (1H, b.s.).

Examples 4 and 5 illustrate the preparation of a compound of formula I(c) from the corresponding compound of formula I(a) by the processes of steps II and III conducted successively.

EXAMPLE 4

Preparation of ethyl 3,3-Dimethyl-5-oxopentanoate from ethyl 3,3-dimethyl-5-phenylthiopentanoate without purification of the intermediate ethyl 5-chloro-3,3-dimethyl-5-phenylthiopentanoate A mixture of 30.0 g (0.113 mole) of ethyl 3,3-dimethyl-5-phenylthiopentanoate and 16.2 g (0.121 mole) of 1-chloro-2,5-pyrrolidinedione in the 150 mL of carbon tetrachloride was stirred at 10°–20° C. for 3 hours. The mixture was filtered, and the filtrate concentrated at room temperature to give a residue.

The residue was added to a mixture of 10 g (0.074 mole) of cupric chloride and 10 g (0.126 mole) of cupric oxide in 150 mL of acetone and 6 mL of water. The reaction mixture was stirred for 1 hour at room temperature, then filtered and the filtrate concentrated to give a residue. The residue was dissolved in ether, washed with an aqueous solution of sodium chloride, concentrated, and the concentrate subjected to distillation to give 15.4 g (72% yield) of ethyl 3,3-dimethyl-5-oxopentanoate, 91% purity (glpc), bp 50°–60°C./40 Pa (0.3 mm Hg).

Methyl 3,3-dimethyl-5-oxopentanoate was prepared from methyl 3,3-dimethyl-5-phenylthiopentanoate in the manner of Example 4, bp 93°–97° C./2130 Pa (16 mm Hg), 86%–90% purity, 52% yield.

EXAMPLE 5

Preparation of ethyl 3,3-dimethyl-5-oxopentanoate from ethyl 3,3-dimethyl-5-phenylthiopentanoate without isolation of the intermediate ethyl 5-chloro-3,3-dimethyl-5-phenylthiopentanoate A mixture of 5.30 g (0.020 mole) of ethyl 3,3-dimethyl-5-phenylthiopentanoate and 2.95 g (0.022 mole) of 1-chloro-2,5-pyrrolidinedione in 30 mL of tetrahydrofuran was stirred at room temperature for 2.5 hours, then filtered.

To the filtrate were added 1 mL of water, 3 g (0.038 mole) of cupric oxide, and 3 g (0.022 mole) of cupric chloride. The mixture was stirred for 1 hour at room temperature, filtered, and the filtrate concentrated. The resulting residue was dissolved in methylene chloride and washed with water. The organic layer was concentrated and subjected to column chromatography on silica gel, eluting with hexane-ethyl acetate gradient mixtures, to give 1.50 g (44% yield) of ethyl 3,3-dimethyl-5-oxopentanoate.

Examples 6 and 7 illustrate preparation of the compound of formula II by the process of step IV.

EXAMPLE 6

Preparation of 3,4-dihydro-4,4-dimethyl-2H-pyran-2-one in toluene

A solution of 11.16 g (0.065 mole) of ethyl 3,3-dimethyl-5-oxopenanoate and 11.2 g (0.073 mole) of phosphoryl chloride in 90 mL of toluene was heated under reflux for 14 hours. The mixture was diluted with ether, washed with an aqueous solution of sodium bicarbonate, dried over anhydrous magnesium sulfate, filtered, and the filtrate concentrated to give, after distillation, 3.29 g (40% yield) of 3,4-dihydro-4,4,-dimethyl-2H-pyran-2-one, bp 105°–110° C./2670 Pa (20 mm Hg).

NMR Data (CDCL$_3$): δ(ppm): 1.10 (6H, s), 2.47 (2H, s), 5.12 (1H, d, J=6 Hz), 6.33 (1H, d, J=6 Hz).

EXAMPLE 7

Preparation of 3,4-dihydro-4,4-dimethyl-2H-pyran-2-one in sulfolane

A solution of 16.98 g (0.10 mole at 93% purity) of ethyl 3,3-dimethyl-5-oxopentanoate and 9.44 g (0.062 mole) of phosphoryl chloride in 10 g of sulfolane was added to 250 g of sulfolane and the whole heated to 200° C. in an oil bath during 50 minutes. The reaction mixture was stirred at 200° C. for 1 hour, then subjected to distillation to give 9.71 g of 3,4-dihydro-4,4-dimethyl-2H-pyran-2-one in 2 fractions: fraction 1, 7.49 g, bp 55° C./400 Pa (3 mm Hg), 95.9% purity (glpc); fraction 2, 2.22 g, bp 55°–120° C./400 Pa, 71.1% purity (glpc).

Example 8 illustrates preparation of the compound of formula II by the process of alternate step IV. The preparation of the compound of formula I(d), 3,3-dimethyl-5-oxopentanoic acid, is illustrated in Example 8(a).

EXAMPLE 8

Preparation of 3,4-dihydro-4,4-dimethyl-2-H-pyran-2-one a. Hydrolysis of ethyl 3,3-dimethyl-5-oxopentanoate To a solution of 1.50 g (8.71 mmol) of ethyl 3,3-dimethyl-5-oxopentanoate in 50 mL of methanol and 1 mL of water was added 1.0 g (17.8 mmol) of potassium hydroxide. The reaction mixture was stirred at room temperature for 41½ hours. The reaction mixture was diluted with water and then made acidic by the addition of aqueous hydrochloric acid. The resulting solution was extracted with methylene chloride repeatedly. The combined organic layer was washed with an aqueous solution of sodium chloride and dried over anhydrous magnesium sulfate. Removal of the solvent afforded 1.05 g of 3,3-dimethyl-5-oxopentanoic acid, 84% crude yield. The nmr spectrum was consistent with the proposed structure.

b. Cyclization of 3,3-dimethyl-5- oxopentanoic acid

A solution of 1.05 g (7.28 mmol) of crude 3,3-dimethyl-5-oxopentanoic acid (from Example 8a) and 1 g (8.4 mmol) of thionyl chloride in 10 mL of benzene was heated under reflux for 6⅔ hours. The reaction mixture was concentrated to give 3,4-dihydro-4,4-dimethyl-2H-pyran-2-one. The nmr spectrum was consistent with the proposed structure.

Examples 9 and 10 illustrate the preparation of a compound of formula III by the process of step V. Example 10 also shows azobisisobutyronitrile to be an ineffective initiator for the addition reaction under the conditions employed.

EXAMPLE 9

Preparation of 5-bromo-3,4,5,6-tetrahydro-4,4-dimethyl-6-trichloromethyl-2-H-pyran-2-one a. Use of light as the initiator A gently refluxing mixture of 2.10 g (16.3 mmol) of of 3,4-dihydro-4,4-dimethyl-2H-pyran-2-one (98% purity) and 10 g (50 mmol) of bromotrichloromethane was irradiated for 6 days. The light source was a 100 watt incandescent light bulb. The reaction mixture was subjected to column chromatography on silica gel eluting with a 10:1 mixture of hexane:ethyl acetate to give 2.79 g (53% yield) of 5-bromo-3,4,5,6-tetrhydro-4,4-dimethyl-6-trichloromethyl-2H-pyran-2-one. The product was purified by sublimation, mp 98.5°–99.5° C.

NMR Data (CDCl$_3$): δ(ppm): 1.23, 1.25 (ss, 6H), 2.67 (2H, bs), 4.12 (1H,d,J=6 Hz), 5.28 (1H,d,J=6 Hz).

b. Use of benzoyl peroxide as the initiator

A mixture of 1.0 g (7.93 mmol) of 3,4-dihydro-4,4-dimethyl-2H-pyran-2-one and 6.29 g (31.7 mmol) of bromotrichloromethane was heated to 100° C. Heating was maintained at 100° C. for 12 hours. During this time 600 mg (2.48 mmol) of benzoyl peroxide was added in six 100 mg portions; a 100 mg portion being added approximately every 2 hours. The reaction mixture was cooled and placed on a silica gel packed chromatography column. Elution was 20:1 hexane:ethyl acetate mixture afforded 1.45 g, 56% yield, of 5-bromo-3,4,5,6-tetrahydro-3,3-dimethyl-6-trichloromethyl-2H-pyran-2-one.

EXAMPLE 10

Preparation of 5-chloro-3,4,5,6-tetrahydro-4,4-dimethyl-6-trichloromethyl-2-H-pyran-2-one To a solution of 2.10 g (0.016 mole) of 3,4-dihydro-4,4-dimethyl-2H-pyran-2-one in 6.5 g (0.042 mole) of carbon tetrachloride was added 100 mg of azobisisobutyronitrile (AIBN), and the reaction mixture stirred at room temperature for 1½ hours. Analysis of the reaction mixture by glpc indicated no adduct had formed. An additional 100 mg of AIBN was added and the temperature was raised to 80° C. and maintained at that level for 2¼ hours. Analysis by glpc showed the desired adduct still had not formed.

Benzoyl peroxide was added in 100 mg or 200 mg portions several times a day while the reaction mixture was heated under reflux for 6 days. The total amount of benzoyl peroxide added was 3.7 g (0.015 mole).

The reaction mixture was cooled and placed on a silica gel packed chromatography column. Elution with a 10:1 hexane:ethyl acetate mixture gave 3.10 g, 70% yield, of 5-chloro-3,4,5,6-tetrahydro-4,4-dimethyl-6-trichloromethyl-2H-pyran-2-one as an oil which crystallized upon standing. Recrysallization from pentane afforded the product as white crystals, mp 83°–84° C.

Analysis for C$_8$H$_{10}$Cl$_4$O$_2$: Calc'd: C, 34.32; H, 3.60; Cl, 50.65; Found C, 34.65; H, 3.59; Cl, 50.51.

Example 11 illustrates preparation of the trihalomethyl bicyclic lactone (1α, 4α, 5α)-6,6-dimethyl-4-trichloromethyl-3-oxabicyclo[3.1.0]hexan-2-one.

EXAMPLE 11

Preparation of (1α, 4α, 5α)-6,6-dimethyl-4-trichloromethyl-3-oxabicyclo[3.1.0]hexan-2-one A solution of 0.4 g (1.43 mmol) of 5-chloro-3,4,5,6-tetrahydro-4,4-dimethyl-6-trichloromethyl-2H-pyran-2-one in 2 mL of tetrahydrofuran was added to a suspension of 0.27 g (2.8 mmol) of sodium tert-butoxide in 2 mL of tetrahydrofuran at 0° C. The mixture was stirred at 0° C. for 2 hours, diluted with an aqueous solution of ammonium chloride, and the whole extracted with methylene chloride. The methylene chloride extract was dried over anhydrous magnesium sulfate and then concentrated. The residue was placed on a silica gel packed chromatography column. Elution with a 100:3 hexane:ethyl acetate mixture gave 0.29 g, 69% yield (1α, 4α, 5α)-6,6-dimethyl-4-trichloromethyl-3-oxabicyclo[3.1.0]hexan-2-one, 83% purity. The proposed structure was confirmed by comparison of the nmr spectrum and glpc retention time with those obtained for an authentic sample prepared by a different method. Analysis by glpc also showed the presence of 13% unreacted 5-chloro-3,4,5,6-tetrahydro-4,4-dimethyl-6-trichloromethyl-2H-pyran-2-one.

We claim:

1. A process for preparing a 5-bromo- or 5-chlorotetrahydropyranone of the formula:

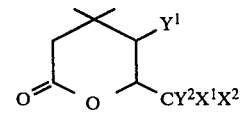

wherein $X^1$ and $X^2$ are the same or different and each is an independently selected halogen atom, a trichloromethyl group, or a trifluoromethyl group, and $Y^1$ and $Y^2$ are independently bromine or chlorine atoms with the proviso that $Y^1$ is a bromine atom when at least one of $X^1$, $X^2$, and $Y^2$ is a bromine atom, which comprises reacting 3,4-dihydro-4,4-dimethyl-2H-pryan-2-one with a halomethane of the formula $Y^1CY^2X^1X^2$ in the presence of an initiator selected from an acyl peroxide, light, and an acyl peroxide and light.

2. The process of claim 1 wherein the acyl peroxide is benzoyl peroxide.

3. The process of claim 1 or 2 wherein the reaction is conducted at elevated temperature.

4. The process of claim 3 wherein the reaction is conducted at a temperature in the range of 50° C. to 200° C.

5. A process for preparing a halomethyl bicyclic lactone of the formula:

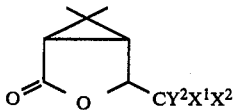

wherein $Y^2$ is a bromine or chlorine atom, and $X^1$ and $X^2$ are the same or different and each is an independently selected halogen atom, a trichloromethyl group, or a trifluoromethyl group which comprises (1) reacting 3,4-dihydro-4,4-dimethyl-2H-pyran-2-one with a halomethane of the formula $Y^1CY^2X^1X^2$ wherein $Y^2$, $X^1$, and $X^2$ are defined as above herein, and $Y^1$ is a bromine or chlorine atom with the proviso that $Y^1$ is a bromine atom when at least one of $Y^2$, $Y^1$, and $X^2$ is a bromine atom, in the presence of an initiator selected from an acyl peroxide, light, and an acyl peroxide and light to form a 5-bromo- or 5-chlorotetrahydropyranone of the formula:

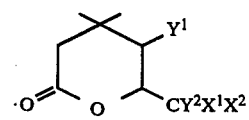

and then (2) dehydrohalogenating the 5-bromo- or 5-chlorotetrahydropyranone in the presence of a base, to bring about ring closure forming the halomethyl bicyclic lactone.

* * * * *

UNITED STATES PATENT AND TRADEMARK OFFICE
CERTIFICATE OF CORRECTION

PATENT NO. : 4,342,694

DATED : August 3, 1982

INVENTOR(S) : Kiyoshi Kondo, Toshiyuki Takashima, Minoru Suda

It is certified that error appears in the above—identified patent and that said Letters Patent is hereby corrected as shown below:

Column 3, formula between lines 25 and 30 reading as follows:

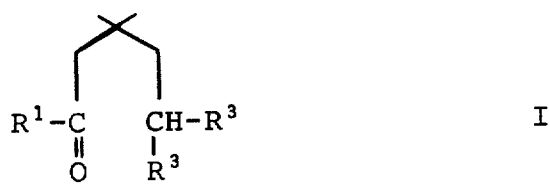

should read:

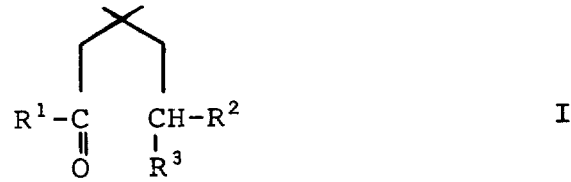

Column 8, line 64, "radial" should read --radical--. Column 10, line 65, "hp 130°" should read --bp 130°--. Column 11, line 56, "in the 150 mL of carbon" should read --in 150 mL of carbon--. Column 13, in heading under EXAMPLE 8, "2-H" should read --2H--; in heading under EXAMPLE 9, "2-H" should read --2H--;

UNITED STATES PATENT AND TRADEMARK OFFICE
CERTIFICATE OF CORRECTION

PATENT NO. : 4,342,694

DATED : August 3, 1982

INVENTOR(S) : Kiyoshi Kondo, Toshiyuki Takashima, Minoru Suda

It is certified that error appears in the above—identified patent and that said Letters Patent is hereby corrected as shown below:

Column 14, in heading under EXAMPLE 10, "2-H" should read --2H--; line 26, "Recrysallization" should read --Recrystallization--. Column 15, line 11, "pryan" should read --pyran--. Column 16, line 16, "$Y^2$, $Y^1$, and $X^2$" should read --$Y^2$, $X^1$, and $X^2$--.

Signed and Sealed this

Twenty-second Day of February 1983

[SEAL]

Attest:

GERALD J. MOSSINGHOFF

Attesting Officer

Commissioner of Patents and Trademarks